(12) United States Patent
Helle et al.

(10) Patent No.: US 9,682,252 B2
(45) Date of Patent: Jun. 20, 2017

(54) ADHESIVE-STIFFENED BRACHYTHERAPY STRAND

(75) Inventors: Kevin Helle, Bartlett, IL (US); Jay Reed, Elk Grove Village, IL (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 1021 days.

(21) Appl. No.: 12/665,878

(22) PCT Filed: Jul. 2, 2008

(86) PCT No.: PCT/US2008/068965
§ 371 (c)(1),
(2), (4) Date: Dec. 21, 2009

(87) PCT Pub. No.: WO2009/006499
PCT Pub. Date: Jan. 8, 2009

(65) Prior Publication Data
US 2010/0324353 A1  Dec. 23, 2010

Related U.S. Application Data

(60) Provisional application No. 60/947,586, filed on Jul. 2, 2007.

(51) Int. Cl.
*A61N 5/10* (2006.01)

(52) U.S. Cl.
CPC .... *A61N 5/1027* (2013.01); *A61N 2005/1023* (2013.01)

(58) Field of Classification Search
CPC .. A61N 5/1001; A61N 5/1002; A61N 5/1007; A61N 5/1014; A61N 5/1027; A61N 2005/101; A61N 2005/1011

USPC ................................................ 600/7, 3, 8
See application file for complete search history.

(56) References Cited

U.S. PATENT DOCUMENTS

| 5,030,195 | A  | * | 7/1991 | Nardi ............................... 600/7 |
| 5,460,592 | A  |   | 10/1995 | Langton et al. |
| 5,667,528 | A  | * | 9/1997 | Colligan .......... A61B 17/06004 606/224 |
| 6,773,390 | B2 |   | 8/2004 | McDaniel |
| 6,932,758 | B1 | * | 8/2005 | McKenzie ........................ 600/8 |
| 7,232,408 | B1 | * | 6/2007 | Fritz .................... A61N 5/1002 600/3 |
| 7,736,292 | B2 | * | 6/2010 | Hermann et al. ................. 600/7 |
| 2003/0181782 | A1 | * | 9/2003 | McDaniel ......................... 600/3 |
| 2004/0186340 | A1 | * | 9/2004 | Reed et al. ....................... 600/7 |

(Continued)

FOREIGN PATENT DOCUMENTS

| EP | 1 346 751 | 9/2003 |
| EP | 1346751 | 9/2003 |

(Continued)

*Primary Examiner* — Charles A Marmor, II
*Assistant Examiner* — Thaddeus Cox
(74) *Attorney, Agent, or Firm* — Grogan, Tuccillo & Vanderleeden, LLP

(57) ABSTRACT

A stranded brachytherapy product and methods of forming a stranded brachytherapy product. The methods includes the step of applying an adhesive to a carrier containing at least one brachytherapy seed so as to, upon curing of the adhesive, impart substantial rigidity to the carrier. Alternatively, the adhesive may be selectively applied so as to provide a deflectable brachytherapy product.

12 Claims, 4 Drawing Sheets

(56) References Cited

U.S. PATENT DOCUMENTS

2006/0142703 A1\* 6/2006 Carter et al. .................. 604/264
2007/0179599 A1\* 8/2007 Brodbeck et al. ........... 623/1.44

FOREIGN PATENT DOCUMENTS

WO          2004/014215     2/2004
WO    WO 2004/082762     9/2004

\* cited by examiner

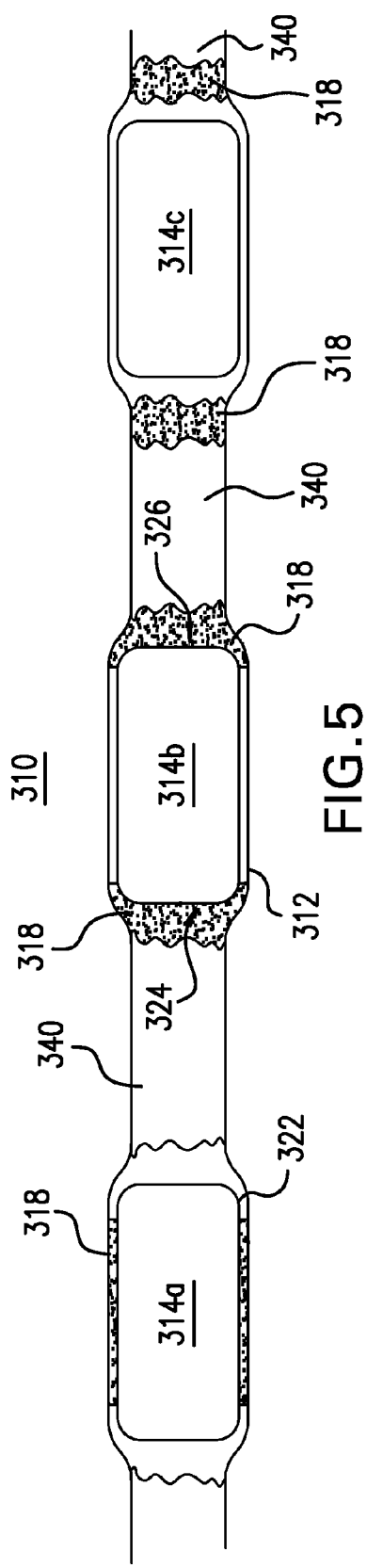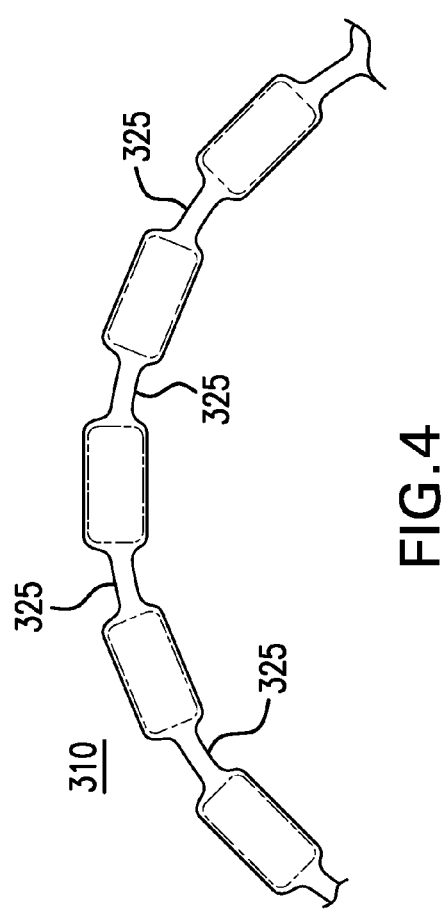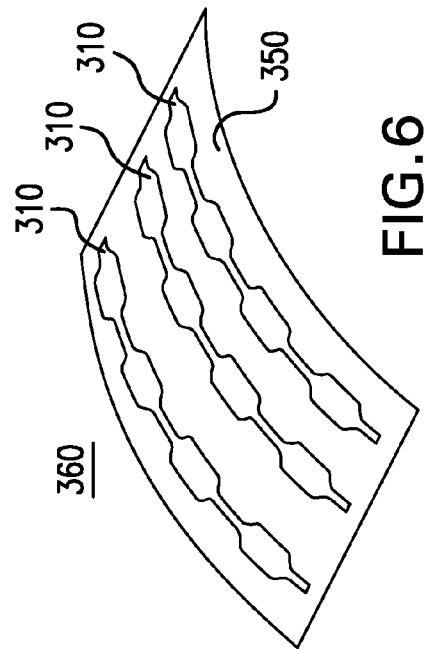

ADHESIVE-STIFFENED BRACHYTHERAPY STRAND

This application is a filing under 35 U.S.C. 371 of international application number PCT/US2008/068965, filed Jul. 2, 2008, which claims priority to application No. 60/947,586 filed Jul. 2, 2007, in the United States the entire disclosure of which is hereby incorporated by reference.

FIELD OF THE INVENTION

The present invention relates to the field of brachytherapy devices. More specifically, the present invention is directed to a stiffened brachytherapy strand and a method for making the same.

BACKGROUND OF THE INVENTION

Brachytherapy strands are cancer therapy devices in which radioactive brachytherapy seeds are provided in an elongate carrier. One such device marketed by the assignee of the present invention is RAPID Strand®, available from its Arlington Heights, Ill. facility. RAPID Strand® is manufactured using a Polyglactin braided carrier. Polyglactin is a mixture of polyglocolide and poly l-lactide and is commonly used as a biologically absorbable material. FIG. 1 depicts a RAPID Strand® product 10 as presently manufactured and sold by GE Healthcare of North Arlington Heights, Ill. The braided carrier 12, clearly seen in FIG. 1, contains radioactive seeds and non-radioactive spacers. The locations of the seeds and spacers are noted by the reference numbers 14 and 16, respectively. The seeds are the cancer therapy components. The spacers are used for optimum seed separation and long axis rigidity of the assembled RAPID Strand®. The seeds and spacers are inserted into the braided carrier, and then the assembled unit is heated in an oven. The oven cycle causes the braided carrier, and seeds and spacers contained within it, to gain enormous strength long axis. This is accomplished by a thermo-induced change in the structure of the Polyglactin material. This heat stiffening process takes considerable time and energy to perform, but is required for finished device assembly functionality.

During implant preparation it is common to cut the standard RAPID Strand® segments into smaller segments for optimum clinical value to the patient. One such method is described in U.S. Pat. No. 5,460,592 assigned to the assignee of the present invention and the contents of which are hereby incorporated by reference as if fully stated herein. When cutting the segments it is not uncommon for the inner components to become somewhat separate from the outer braid. Heating the end, after cutting the segment, can help in retaining the components in the braided carrier material. It should be noted that the seed components themselves are made of titanium and have no physical connection to the braided carrier or the spacers. The seeds are contained within the heat-stiffened suture and between the spacers. Long axis rigidity is accomplished by having components (seeds and spacers) stacked end to end within a very tight braided material.

There is therefore a need for an alternative method for imparting long-axis stiffness, and end spacer retention when cut, to a brachytherapy strand. There is also a need for an elongate brachytherapy strand having regions of longitudinal stiffness adjacent regions of considerably reduced longitudinal stiffness to facilitate deflection of the strand when used for applications in which it is desired for the strand to more closely conform to deflectable tissue, such as lung tissue during the process of inhalation and exhalation.

SUMMARY OF THE INVENTION

The present invention utilizes chemical adhesion instead of the current thermal process. The new method will be used to stiffen the RAPID Strand assembled unit during manufacturing using an adhesive, such as cyanoacrylate. The new method will similarly allow a technician to end-seal the cut RAPID Strand segments during implant preparation using an adhesive, such as cyanoacrylate. In one embodiment, the present invention provides an elongate strand having distinct regions about the seeds where the carrier is adhered to either the seeds themselves, to spacers extending within the carrier between the seeds, or where the carrier closes off the carrier adjacent to each seed so as to fix the seed in place within the carrier. In an another embodiment, the present invention provides an elongate strand having relatively stiff regions where the seeds are fixed into place adjacent to relatively deflectable regions where the carrier may be deflected so as to give an ability to shape the strand to non-linear or non-planar tissue applications.

During the manufacturing process, the assembled strand is passed through an adhesive vapor chamber where the hydroscopic Polyglactin will absorb the adhesive vapor creating chemical adhesion between the braided carrier, the seeds and any spacers employed within the carrier. This process can also be done by dipping, spraying or any other means of applying an extremely small and controlled amount of adhesive to the assembly. In one embodiment of the present invention, the adhesive so applied is cyanoacrylate.

Additionally, during the segmentation of strand, the exposed ends of the cut strand segment is dipped, sprayed, or by any other means of applying an extremely small and controlled amount of adhesive to the cut ends of the segment so as to seal the segment ends.

BRIEF DESCRIPTION OF THE DRAWINGS

FIG. 4 depicts a further brachytherapy product of the present invention.

FIG. 5 illustrates alternative methods for affixing a seed within a carrier so as to provide a brachytherapy product of FIG. 4.

FIG. 6 depicts a brachytherapy patch of the present invention.

DETAILED DESCRIPTION OF THE PREFERRED EMBODIMENTS

The initial loading of the brachytherapy strand may be performed by the current method, such as seeds and spacers loaded into a hollow suture material manually or by using an automated or semi-automated manufacturing process. As is known in the art, the spacers may be of uniform length or of varying lengths as dictated by a particular dosimetry plan.

The carrier assembly (i.e., the carrier loaded with seeds and, optionally, spacers) will be exposed to an adhesive by either exposing the assembled unit to a spray type coating, exposing the assembled unit to a vapor stream, dipping the assembled unit in a bath, or using the hydroscopic polyglactin material of the carrier to induce adhesive transfer. Desirably the adhesive used will be a medical grade cyanoacrylate or any other suitable adhesive.

Alternatively, the carrier material may only be loaded with seeds spaced apart as desired by a particular dosimetry plan. The adhesive will stiffen the carrier between the seed components (in the void areas), resulting in a medical device with less bio-absorbable material (there would be no spacers). Without spacers the device may be assembled with considerably less time and cost.

The devices and methods of the present invention can eliminate or reduce the possibility of seeds becoming dislodged from the strand as a result of cutting the strand. Similarly, the devices and methods of the present invention can also eliminate or reduce the possibility of spacers becoming dislodged from the stand as a result of cutting. Additionally, it may not be necessary to even use spacers in a strand of the present invention. The devices and methods of the present invention provide a strand having the desired long-axis stiffness. The present invention also allows the elimination of using an oven in the manufacturing process with its attendant validation requirements. The rigidity of devices of the present invention will be maintained even in moist conditions.

Figure 1:
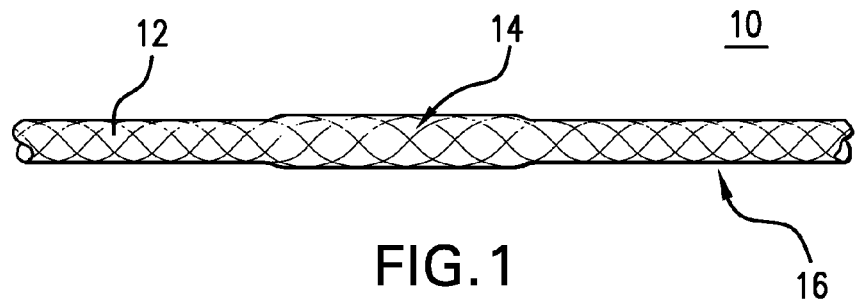
FIG. 1 depicts a close-up view of a section of a brachytherapy product of the prior art.
Figure 2:
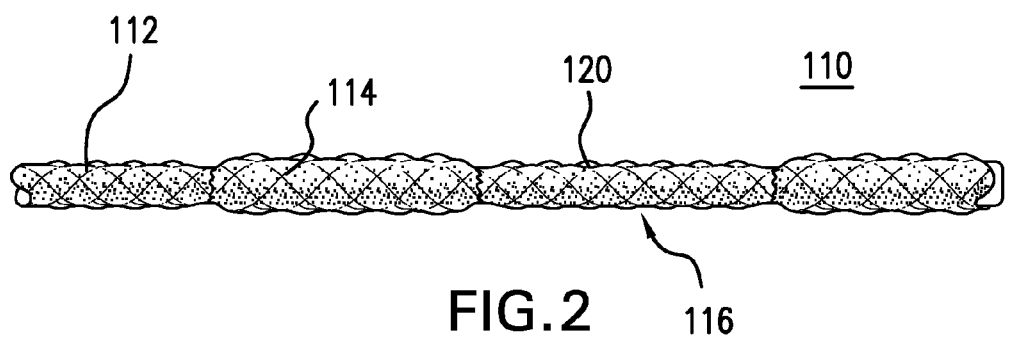
FIG. 2 depicts a section of a brachytherapy product of the present invention.

FIG. 2 depicts a brachytherapy strand 110 of the present invention. Strand 110 includes an elongate carrier material 112 loaded with radioactive seeds 114 and inert spacers 116. Carrier 112 is a hollow polyglactin braid. The lead lines from reference numbers 112 and 114 indicate the respective location of the seeds and spacers within the hollow interior of carrier 112. A medical grade cyanoacrylate adhesive material has been applied to carrier 112 so as to affix the seeds 114 and spacers 116 therein and to impart long-axis stiffness to strand 110. FIG. 2 shows that the applied adhesive may form localized protrusions 120 on the surface of carrier 112. The protrusions 120 can serve as anchors for strand 110 once implanted in tissue. The protrusions 120 thus help prevent migration of strand 110 after implantation.

Figure 3:
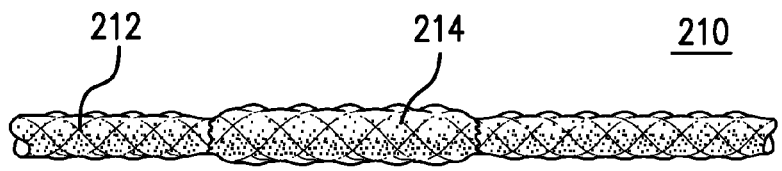
FIG. 3 depicts a close-up view of a section of the brachytherapy product of FIG. 2.

FIG. 3 depicts an alternate brachytherapy strand 210 of the present invention. Strand 210 includes an elongate carrier material 212 loaded with radioactive seeds 214. Carrier 212 is also a hollow polyglactin braid. The lead lines from reference numbers 212 indicate the location of the seeds within the hollow interior of carrier 212. A medical grade cyanoacrylate adhesive material has been applied to carrier 212 so as to affix seeds 214 therein and to impart long-axis stiffness to strand 210.

FIGS. 4 and 5 depict a further brachytherapy strand 310 of the present invention. Strand 310 includes a carrier material 312 loaded with a number of radioactive seeds 314. Carrier material 312 may be hollow polyglactin braid or suture. Strand 310 is characterized by its regions 325 between adjacent seeds 314 where the carrier material 312 is able to deflect so as to allow the strand to conform to non-linear or non-planar applications or tissue. For example, as shown in FIG. 6, strand 312 may be incorporated into or onto a planar surgical mesh 350 so as to provide an implantable and deflectable brachytherapy mesh patch 360. Patch 360 is suitable for implantation, for example, along the abdominal wall or over lung tissue. The deflectability of the strands 310 used in the construction of patch 360 will allow the patch to more easily deflect with the tissue, reducing patient strain while also reducing tension between patch 360 and the tissue it is implanted on as the tissue deflects during movement. Additionally, by allowing a technician to attach or otherwise affix pre-formed brachytherapy strands to mesh 350, patch 360 may be constructed quickly so as to reduce operator exposure to the radioactive seeds during construction.

FIG. 5 illustrates alternative methods for affixing a seed 314 within carrier 312 so as to provide a brachytherapy product such as strand 310 of FIG. 4. While FIG. 5 depicts different methods for affixing the seeds 314 within the same carrier 312, it is generally contemplated that any particular strand 310 will employ only a single one of such methods such that each adjacent seed will be affixed in the same manner. Thus, for illustrative purposes, all of the methods are shown in a single strand. Seed 314a is shown affixed to carrier 312 by adhesive 318 applied through carrier 312 so as to contact the elongate outer surface 322 of seed 314. Alternatively, seed 314b is shown affixed to carrier 312 by adhesive 318 applied through carrier 312 so as to contact the opposed ends 324 and 326 of seed 314. Where each of these methods seek to apply the adhesive so as to directly contact the seed, the present invention also contemplates, as shown for seed 314c, that adhesive 318 may be applied through carrier 312 so as to seal-off the internal passageway 340 of carrier 312 to either side of seed 314c. Note that seed 314c is not adhered to carrier 312 as much as it is affixed within it between successive adhesive blockages. Each of these methods result in a region 340 between each adjacent seeds 314 where there is no adhesive applied so that the carrier 312 is free to deflect in that region so as to allow greater flexibility to strand 310.

Figure 7:
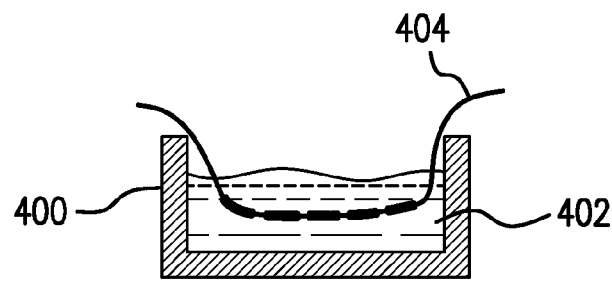
FIG. 7 depicts a first method of applying an adhesive to the carrier material of a stranded brachytherapy product of the present invention.

The present invention contemplates several methods for applying an adhesive, desirably cyanoacrylate, onto a carrier assembly (a carrier loaded with seeds and, optionally, spacers). FIG. 7 depicts a first method of applying an adhesive to the carrier material of a stranded brachytherapy product of the present invention. In this method, an open-top tank 400 holds a volume of liquid adhesive 402, desirably cyanoacrylate. A carrier assembly 404 is dipped into the liquid adhesive 402 so that the carrier about the loaded seeds is coated with the adhesive. The coated carrier assembly is then removed from the adhesive pool and held in tension until the adhesive thereon cures. Excess lengths of carrier material may be cut-away and, if necessary, the exposed ends of the carrier may be sealed by adhesive.

Figure 8:
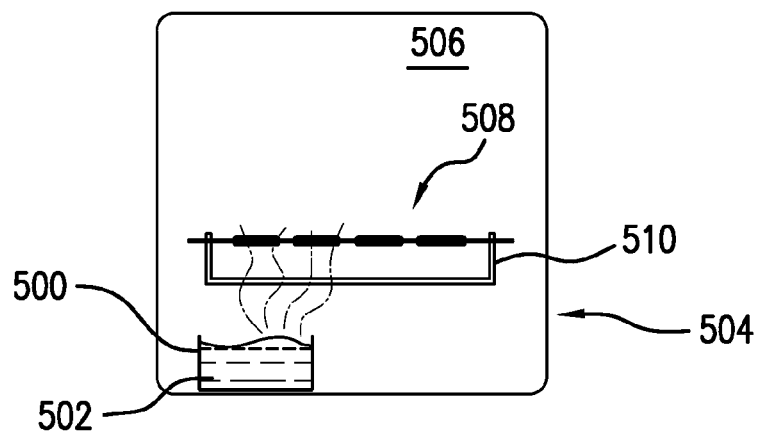
FIG. 8 depicts a second method of applying an adhesive to the carrier material of a stranded brachytherapy product of the present invention.

FIG. 8 depicts a second method of applying an adhesive to the carrier material of a stranded brachytherapy product of the present invention. In this method, an open-top container 500 holds a volume of liquid adhesive 502. Container 500 is placed in a sealed chamber 504 which defines a chamber cavity 506. A carrier assembly 508 held in tension by frame 510 is placed in chamber cavity 506. Either a vacuum is drawn in cavity 506 or cavity 506 is filled with an inert gas so as to cause vapors from adhesive 502 to coat carrier assembly 508. The coating applied to carrier assembly 508 need not be a continuous layer of adhesive. After sufficient time to coat as desired, frame 510 and carrier assembly 508 are placed in a normal atmosphere so that the applied adhesive cures.

Figure 9:
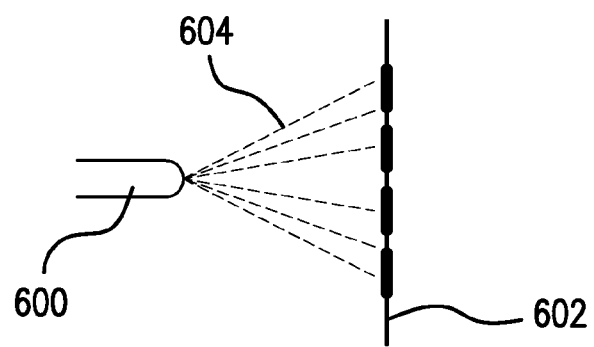
FIG. 9 depicts a third method of applying an adhesive to the carrier material of a stranded brachytherapy product of the present invention.

FIG. 9 depicts a third method of applying an adhesive to the carrier material of a stranded brachytherapy product of the present invention. In this method a nozzle 600 is connected to a source of liquid adhesive, desirably cyanoacrylate, under pressure. A carrier assembly 602 is held in tension adjacent to nozzle 600 and a sprayed or atomized adhesive 604 is applied to the carrier assembly. Once again, it not necessary to completely coat the outside of the carrier assembly with the adhesive. The adhesive is allowed to cure.

Figure 10:
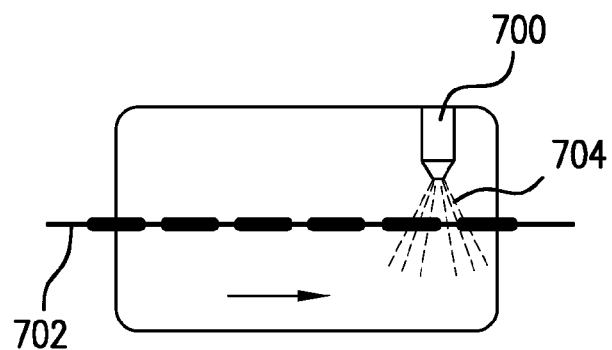
FIG. 10 depicts a fourth method of applying an adhesive to the carrier material of a stranded brachytherapy product of the present invention.

FIG. 10 depicts a fourth method of applying an adhesive to the carrier material of a stranded brachytherapy product of the present invention. In this method a nozzle 700 is connected to a source of liquid adhesive, desirably cyanoacrylate. A carrier assembly 702 is drawn, under tension, below the nozzle so that the adhesive 704 is either sprayed or dripped onto the moving carrier assembly. It is not necessary to fully coat the outside of the carrier assembly. As the carrier assembly continues past the nozzle, the applied adhesive cures and the desired brachytherapy strands are cut to length.

Figure 11:
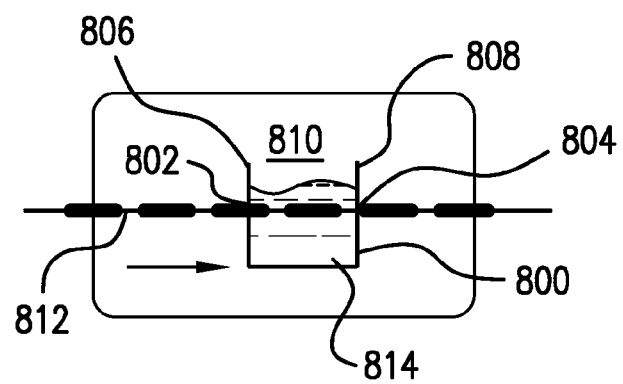
FIG. 11 depicts a fifth method of applying an adhesive to the carrier material of a stranded brachytherapy product of the present invention.

FIG. 11 depicts a fifth method of applying an adhesive to the carrier material of a stranded brachytherapy product of the present invention. In this method, a container 800 is provided having transverse holes 802 and 804 formed in opposing upstanding walls 806 and 808, respectively. Container 800 defines a container cavity 810. Carrier assembly 812 is drawn, under tension through holes 802 and 804 so as to traverse cavity 810. While carrier assembly 812 is drawn through cavity 810, a liquid adhesive 814, desirably cyanoacrylate, is provided to cavity 810 so as to coat carrier assembly 812. Hole 804, being the exit hole from cavity 810, is desirably sized to provide a sliding contact with carrier assembly 812 so as to remove any excess adhesive applied thereto. Upon curing of the adhesive applied to assembly 812, strands may be cut to length.

Figure 12:
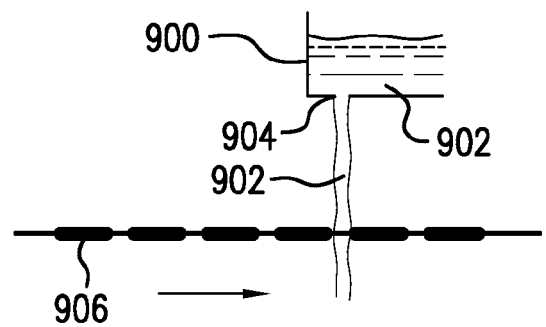
FIG. 12 depicts a sixth method of applying an adhesive to the carrier material of a stranded brachytherapy product of the present invention.

FIG. 12 depicts a sixth method of applying an adhesive to the carrier material of a stranded brachytherapy product of the present invention. In this method, a container 900 holding liquid adhesive 902, desirably cyanoacrylate, is provided. Container 900 defines a flow port 904 through which adhesive 902 may flow. A carrier assembly 906, under tension, is drawn through stream of the falling adhesive. Once the adhesive applied to the carrier assembly 906 cures, brachytherapy strands may be cut to length.

While the particular embodiment of the present invention has been shown and described, it will be obvious to those skilled in the art that changes and modifications may be made without departing from the teachings of the invention. The matter set forth in the foregoing description and accompanying drawings is offered by way of illustration only and not as a limitation. The actual scope of the invention is intended to be defined in the following claims when viewed in their proper perspective based on the prior art.

What is claimed is:

1. A stranded brachytherapy product comprising:
    an elongate hollow carrier of biologically absorbable material having opposed first and second ends and defining an elongate seed cavity therein;
    at least one radioactive brachytherapy seed positioned within said seed cavity,
    an adhesive applied along an outer surface and absorbed into the hollow of said carrier so as to, upon curing of said adhesive, impart substantial long axis stiffness and rigidity to said carrier;
    at least one spacer element positioned within said cavity wherein a portion of said adhesive penetrates said carrier so as to adhere to said at least one spacer or at least one brachytherapy seed; and
    wherein at least one region of said carrier adjacent to said at least one seed is free of adhesive so as to permit deflection of said carrier at the at least one region, and
    wherein a portion of said adhesive protrudes out from the outer surface of said carrier so as to form protrusions on said outer surface.

2. A stranded brachytherapy product of claim 1, wherein said adhesive comprises a medically-suitable formulation of cyanoacrylate.

3. A stranded brachytherapy product of claim 1, wherein said adhesive is applied at multiple locations on said carrier.

4. A stranded brachytherapy product of claim 1, wherein said carrier comprises an elongate hollow suture material.

5. A brachytherapy patch comprising:
    a planar surgical mesh and
    at least one stranded brachytherapy product of claim 1 adhered or otherwise affixed to said mesh.

6. A method of forming a stranded brachytherapy product comprising the steps of:
    loading at least one brachytherapy seed into a seed cavity of an elongate carrier,
    applying an adhesive along an outer surface and absorbed into a hollow of said carrier so as to, upon curing of said adhesive, impart substantial long axis stiffness and rigidity to said carrier,
    penetrating said carrier with said adhesive so as to seal closed the seed cavity of said carrier at least at one location adjacent to said at least one seed,
    wherein at least one region of said carrier adjacent to said at least one seed is free of adhesive so as to permit deflection of said carrier at the at least one region, and
    wherein a portion of said adhesive is applied to said outer surface of said carrier so as to form at least one projection on said outer surface of said carrier.

7. A method of claim 6, wherein said applying step further comprises the step of:
    passing the loaded carrier through a vapor chamber providing a vapor containing said adhesive.

8. A method of claim 6, wherein said applying step further comprises the step of:
    dipping said carrier into a bath of said adhesive.

9. A method of claim 6, wherein said applying step further comprises the step of:
    spraying said adhesive onto said carrier material.

10. A method of claim 9, wherein said spraying step further comprises the step of:
    providing said adhesive onto said carrier in droplets so as to form said at least one projection on the outer surface of said carrier.

11. A method of claim 6, wherein said applying step further comprises the step of:

affixing said at least one seed at a location within the seed cavity.

12. A method of claim 11, wherein said applying step further comprises the step of:

sealing said seed cavity at locations immediately to either side of said at least one seed.

* * * * *